(12) United States Patent
Niwa et al.

(10) Patent No.: US 6,659,029 B2
(45) Date of Patent: Dec. 9, 2003

(54) METHOD OF PLANTING TREES AND GROWING PLANTS

(75) Inventors: Kozo Niwa, 4-4, Asahimachi, Tosashimizu-shi, Kochi (JP); Yoshinori Sasaki, Hita (JP)

(73) Assignee: Kozo Niwa, Kochi (JP)

( * ) Notice: Subject to any disclaimer, the term of this patent is extended or adjusted under 35 U.S.C. 154(b) by 0 days.

(21) Appl. No.: 09/975,629

(22) Filed: Oct. 11, 2001

(65) Prior Publication Data
US 2002/0069799 A1 Jun. 13, 2002

(30) Foreign Application Priority Data
Oct. 11, 2000 (JP) ........................ 2000-310811

(51) Int. Cl.$^7$ ............................... A01C 7/00
(52) U.S. Cl. ...................... 111/200; 111/900
(58) Field of Search ............ 47/101, DIG. 58; 111/100, 200, 104, 105, 919, 900; 800/200, 205, 230, 260, 289; 536/24.3; 435/6, 410, 430

(56) References Cited

U.S. PATENT DOCUMENTS

| | | |
|---|---|---|
| PP7,924 P | 7/1992 | Niwa et al |
| 5,908,978 A * | 6/1999 | Amerson et al. ........... 800/319 |
| 6,294,715 B1 * | 9/2001 | Barham et al. ............. 800/306 |

OTHER PUBLICATIONS

Nov. 1, 1997 Abstract of "The detection and conservation of tetraploid sugi, *Cryptomeria japonica* D. Don." Hideo Kikuti Bulletin of the Forestry and Forest Products Research Institute vol. 0, No. 374 pp. 83–113, 1998.
Abstract of "Somatic chromosome numbers of colchicine–treated Shinano walnut" Masao Yajima et al. Journal of the Japanese Society for Horticultural Science vol. 65 No. 4 pp. 677–683, 1997.
Abstract of "In vitro propagation of tetraploid European Aspen" Premysl Mikes et al. Lesnictvi (Prague) vol. 39, No. 5 pp. 184–186, 1993.
Abstract of "Cytogenetical Estimation of the Oak Trees of Different Selection Categories" A.K. Butorina Genetika vol. 25, No. 2 pp. 301–309, 1989.
May 25, 1999 Abstract of "Cool Temperature Lawn Having Hot Tolerance and Its Creation" WPI/Derwent.
Abstract of "Method of Obtaining Miotic Polyploids of Coniferous Plants" Ekaterina M. Gulyaeva et al. WPI/Derwent, 1999.
Progress in the biotechnology of trees N. Hammatt World Journal of Microbiology and Biotechnology vol. 8, No. 4 pp. 369–377, 1992.

* cited by examiner

Primary Examiner—Robert E. Pezzuto
(74) Attorney, Agent, or Firm—Jordan and Hamburg LLP

(57) ABSTRACT

Inhibition of forest damage exerts by ultraviolet rays. By selecting species having triploid or tetraploid of chromosomes and afforestating to form the ultraviolet resistant forest by forming the artificial forest.

11 Claims, 1 Drawing Sheet

METHOD OF PLANTING TREES AND GROWING PLANTS

BACKGROUND OF THE INVENTION

The present invention relates to a plant growing technique such as planting trees, and more specifically, to a technique of selectively growing young trees or the like which is resistant to ultraviolet rays so that vegetation such as a forest which is resistant to ultraviolet rays can be reliably obtained.

There has been discussed recently on the issue of ultraviolet rays problem on earth. Because especially the ozonosphere of stratosphere surrounding the earth is recently destroyed, the ultraviolet rays come to the earth from outside and has been confirmed to show bad influence on biology on the earth.

For example, as to human body, there has been reported the increment of damage due to ultraviolet rays, and it has been confirmed that the increase of skin cancer cases are due to increment of radiation by ultraviolet rays. Thus damage based on ultraviolet rays was thought to cause the occurrence of active oxygen. Niwa, one of the present inventors, has studied their pharmacological, biochemical properties on several damages caused by active oxygen for long years.

SUMMARY OF THE INVENTION

The real states that damages based on conventional ultraviolet rays are mainly by studying on their effects on human body as the main topics. In contrast to this, the present inventors has reached to the conclusion that ultraviolet rays have also given big damages on forest.

It is disclosed that the biggest reason that damage forwarded to the forest is acid rain's exertion. For example, at Schwarzwald district in Germany, a report dealt with big damage covered large area where so many trees uprightly withered by acid rain. The acidic oxides such as sulfur-containing oxides existed in the industrial burning, were dissolved in the rain drops and resulting become acidic rain.

The investigation on the damage was performed repeatedly by the present inventors who visited the damaged domestic forest and obtained many results.

The present inventors observed the damage of the domestic forest by repeatedly visiting several places of the damaged forest in several districts. After a detailed investigation about the observed states, the present inventors investigated that it is possible that the factors other than acid rain strongly concerned with abnormal phenomena of withered trees found largely in the forest found. The damages may possibly be due to ultraviolet rays found as the main factor in relating to forest damage to our further research result.

There is not so far examined before on the effect of ultraviolet rays exerting the forest damage. As the present inventors viewed the forest damage state due to ultraviolet rays, it is necessary to take a practical measure rapidly to inhibit such forest damage. Because enlarging the depletion of ozonosphere and the ultraviolet radiation increasing of world scale, it is a top urgent action to be taken for inhibiting the damage caused by ultraviolet rays during the several factors exerting to forest damage. If the damages were dealt with no policy, in the future, the forest trees withered uprightly worldwide by the ultraviolet rays. And the prophecy is forest will be disappeared with global scale.

The object of the present invention is to suppress the damage on forest caused by ultraviolet rays.

The man-planted forest of the present invention is characterized in that is constituted by planting seedling having multiploid (TASUSBI in Japanese). The chromosome number of the seedlings is triploid or tetraploid. The seedlings are those of a conifer. The seedlings of a conifer are seedlings selected from the group consisting of Japanese cedar and Japanese cypress. The chromosome number of the seedling is obtained by increasing the number of chromosomes such as by breeding and mutation.

The method of planting trees of the present invention is characterized in that it comprises the steps of: selecting seedlings having multiploid chromosome; and planting the selected seedlings. The chromosome number of the seedlings is triploid or tetraploid. The seedlings are those of a conifer. The seedlings of a conifer are seedlings of Japanese cedar or Japanese cypress. The chromosome number of the seedlings is obtained by means of increasing the number of chromosomes such as breeding and mutation. The method of growing plants of the present invention is characterized in that it comprises the step of artificially forming vegetation which is significantly resistant to ultraviolet rays, as compared with vegetation constituted of diploid plants, by selectively growing plants whose chromosome number exceeds the basic number intrinsic of the species.

In this specification, "multiploid" (TASUSEI in Japanese) means those chromosomes with more than 3-fold of fundamental chromosome by multiplying integral number of chromosome, and those chromosomes possessing more or less, by 1 to few, than the basic number is acquired by the species. Furthermore it should be noted that haploid, or diploid which is normally observed in plants, is not included into the scope defined by the aforementioned "multiploid".

DESCRIPTION OF THE PREFERRED EMBODIMENTS

Figure 1:
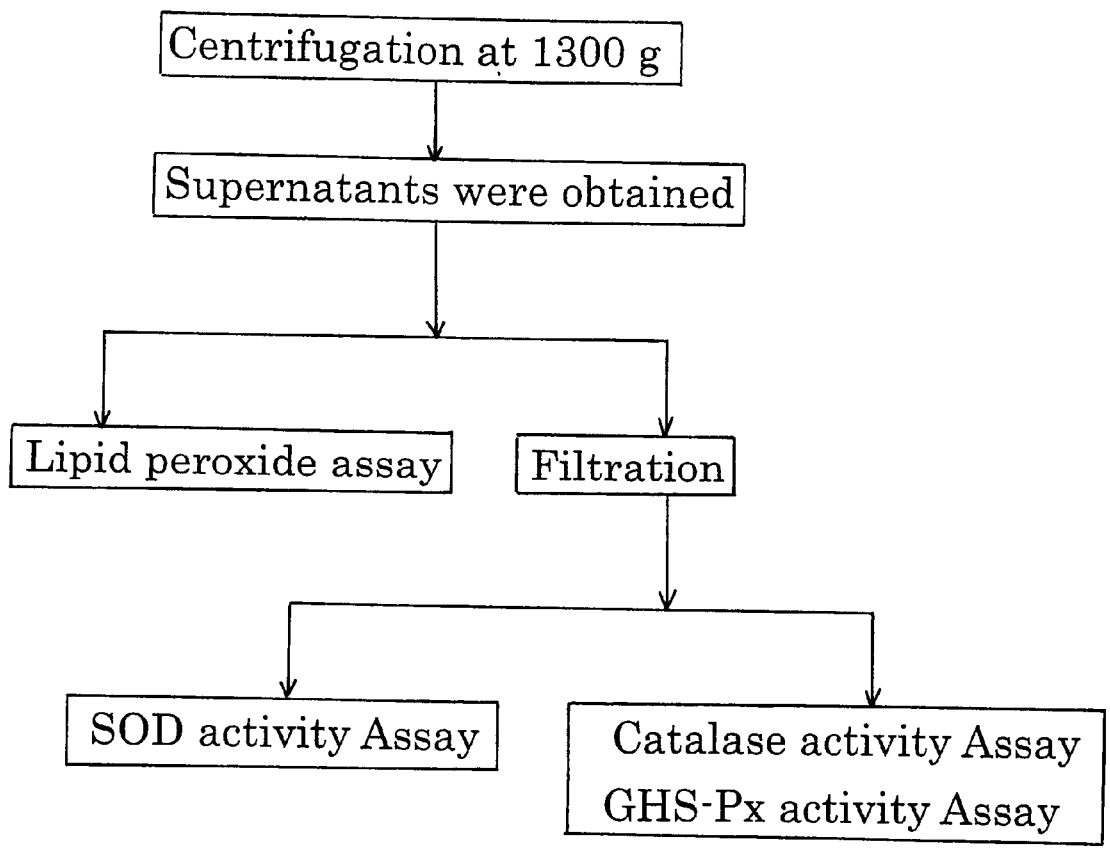
FIG. 1 is a flow chart showing the solution centrifugation procedure.

The following describes the examples state of performance and details.

The seedling used in man-planted forest, method of planting trees and method of growing plants in this invention is ultra-violet-resistant (including "UV-resistant" abbreviation afterwards). The afforestation by choosing UV-resistant seedling and a man-planted forest with capacity of possessed resistant property against ultra-violet rays.

Upon selection of seedling possessing UV-resistant property, a standard of multiploid (TASUSEI) chromosomes acquired by the seedling is adopted for selection. The multiploid stated here means the case that the seedling having more than triploid chromosomes.

Such standard is suggested for the first time by the present inventors. Trees having multiploid chromosomes possess their resistance against ultraviolet rays than the diploid trees normally observed. In the man-planted forest formed by afforesting UV-resistant seedling, the occurrences of damage from ultraviolet rays observed in the trees having diploid chromosomes will be inhibited effectively. The abnormal phenomena such as tree withering uprightly, dying of leaves of evergreens, deciduous trees their leaves fall at the season of not falling. This abnormal phenomena is thought to be caused by ultraviolet rays, and this can be inhibited.

For description of several kinds of tree and ascertain the efficacy of this invention in the examples, the following article and discussion are given in detail.

EXAMPLE

In the Example, those leaves of plants described in items (1)–(3) below, were collected and subjected to experiment about ultraviolet resistance (UV-resistance).

(1) Rice

For a comparison of samples, the rice leaf was used. Rice, a monocotyledonous plant is well known for its resistance against ultraviolet rays. The rice leaf samples used in the experiment were grown at Tosashimizu city, Kochi Prefecture, Shikoku, Japan. The rice leaf were collected from five places at Tosashimizu city and subjected to measurement of enzyme activity, etc. by the method described later.

(2) Osmunda

Leaves of osmunda which is spontaneously growing in Tosashimizu, Japan, were collected as the object of experiment. As well known that osmunda, a fern, its plant evolutionary is old than other trees. Many reports dealt with the cases that osmunda possesses the adaptability to the environmental conditions by acquiring the multiplying ploid of chromosome of the species.

(3) Gymnosperms such as Black Pines etc.

As a sensitive plant to ultraviolet rays, the leaves of gymnosperms were included into the objects of experiment. In Tables 1–4 of this Example, KUROMATSU tree (English name: Japanese black pine tree), SUGI tree (English name: Japanese cedar) and HINOKI tree (English name: Japanese cypress) spontaneously growing in mountain of Japan, their leaves were adopted for the object of experiments. These leaf samples of black pine, cedar and cypress trees were collected from the places and numerated as shown in Tables 1–4.

Black pine tree (hereinafter abbreviated as "control black pine) is known to be sensitive to common UV rays and black pines resistant to UV rays (hereinafter abbreviated as "UV-resistant black pine) were separately described in Table 1, assays for SOD activity, GSH-Px activity and lipid peroxide levels were performed.

Furthermore, as demonstrated in Tables 5 and 6, measurements for triploid species and tetraploid species resulting from crossing and mutation were also performed.

TABLE 1

Comparison of lipid peroxide levels, SOD and glutathione peroxide (GSH-Px) activities between UV resistant Japanese black pines and UV sensitive Japanese black pines.

| Sample name | SOD activity (unit/gr) | GSH-Px activity (unit/gr) | Lipid peroxide Levels (n mol/gr) |
|---|---|---|---|
| UV resistant Japanese black Pines | | | |
| Nakamikata-73 | 391 ± 46 | 0.0215 ± 0.0032 | 18.0 ± 2.1 |
| Tosashimizu-63 | 225 ± 29 | 0.0171 ± 0.0021 | 16.7 ± 2.0 |
| Ooita-8 | 201 ± 28 | 0.0269 ± 0.0029 | 18.2 ± 2.3 |
| Ei-425 | 358 ± 46 | 0.0190 ± 0.0022 | 20.7 ± 2.8 |
| Tsuyasaki-50 | 461 ± 73 | 0.0236 ± 0.0035 | 22.2 ± 3.3 |
| Misaki-90 | 346 ± 41 | 0.0230 ± 0.0036 | 23.4 ± 3.0 |
| Namikata-73 | 456 ± 59 | 0.0331 ± 0.0052 | 22.0 ± 3.7 |
| Tanabe-54 | 367 ± 44 | 0.0214 ± 0.0027 | 20.5 ± 2.8 |
| Yasu-37 | 195 ± 21 | 0.0236 ± 0.0033 | 18.4 ± 2.9 |
| Yoshida-2 | 817 ± 106 | 0.0246 ± 0.0039 | 23.5 ± 2.8 |
| Sendai-290 | 245 ± 31 | 0.0233 ± 0.0039 | 19.9 ± 2.7 |
| Mitoyo-103 | 896 ± 107 | 0.0276 ± 0.0030 | 24.1 ± 3.8 |
| Average | 423 ± 56* | 0.0237 ± 0.0035 | 20.6 ± 3.6 |
| Control UV sensitive Japanese black pines | | | |
| No.1 | 252 ± 30 | 0.0177 ± 0.0023 | 20.5 ± 3.2 |
| No.2 | 99 ± 11 | 0.0142 ± 0.0018 | 22.9 ± 4.1 |
| No.3 | 141 ± 18 | 0.0198 ± 0.0031 | 21.1 ± 2.9 |
| No.4 | 356 ± 46 | 0.0206 ± 0.0037 | 21.9 ± 3.5 |
| No.5 | 352 ± 42 | 0.0198 ± 0.0017 | 18.7 ± 2.4 |
| Average | 240 ± 37* | 0.00184 ± 0.0031 | 21.0 ± 3.8 |

*$P < 0.01$ between UV resistant and sensitive black pine trees.

TABLE 2

Comparison of lipid peroxide levels, SOD and GSH-Px activities in Japanese cypress triploid

| | | Sample name | Poly ploidy | SOD activity (unit/gr) | GSH-Px activity (unit/gr) | Lipid peroxide Levels (n mol/gr) |
|---|---|---|---|---|---|---|
| Japanese cypress | Control diploids | B-4 | 2X | 472 ± 56 | 0.0180 ± 0.0023 | 19.9 ± 2.3 |
| | | B-11 | 2X | 614 ± 73 | 0.0155 ± 0.0020 | 21.3 ± 2.9 |
| | | B-13 | 2X | 552 ± 71 | 0.0019 ± 0.0003 | 27.5 ± 3.0 |
| | | D-4 | 2X | 874 ± 104 | 0.0107 ± 0.0016 | 26.4 ± 3.9 |
| | | D-9 | 2X | 549 ± 65 | 0.0028 ± 0.0003 | 25.7 ± 3.5 |
| | | D-12 | 2X | 683 ± 88 | — | 28.8 ± 3.7 |
| | | D-14 | 2X | 466 ± 60 | 0.0077 ± 0.0012 | 22.9 ± 3.6 |
| | | Average | | 601 ± 46† | 0.0094 ± 0.0002 | 24.6 ± 4.1 |
| | Artificial Triploids | A-8 | 3X | 479 ± 71 | 0.0123 ± 0.0017 | 24.7 ± 3.4 |
| | | A-13 | 3X | 543 ± 70 | 0.0119 ± 0.0015 | 27.8 ± 3.6 |
| | | A-24 | 3X | 685 ± 89 | 0.0014 ± 0.0002 | 28.1 ± 4.4 |
| | | A-54 | 3X | 505 ± 70 | 0.0058 ± 0.0008 | 22.7 ± 3.1 |
| | | A-58 | 3X | 558 ± 55 | 0.0079 ± 0.0012 | 21.1 ± 2.3 |
| | | A-72 | 3X | 674 ± 74 | — | 19.1 ± 2.4 |
| | | A-77 | 3X | 482 ± 77 | 0.0065 ± 0.0011 | 20.8 ± 3.3 |
| | | C-6 | 3X | 559 ± 61 | 0.0100 ± 0.0012 | 21.5 ± 2.5 |
| | | C-22 | 3X | 548 ± 65 | 0.0126 ± 0.0017 | 19.5 ± 2.3 |
| | | C-37 | 3X | 580 ± 69 | 0.0055 ± 0.0008 | 22.2 ± 2.8 |
| | | C-50 | 3X | 589 ± 82 | — | 21.1 ± 3.1 |
| | | C-55 | 3X | 577 ± 75 | — | 20.9 ± 2.7 |
| | | C-60 | 3X | 624 ± 74 | — | 19.4 ± 2.3 |
| | | C-140 | 3X | 646 ± 83 | 0.0026 ± 0.0004 | 19.9 ± 2.7 |

TABLE 2-continued

Comparison of lipid peroxide levels, SOD and GSH-Px activities in Japanese cypress triploid

| Sample name | Poly ploidy | SOD activity (unit/gr) | GSH-Px activity (unit/gr) | Lipid peroxide Levels (n mol/gr) |
|---|---|---|---|---|
| C-225 | 3X | 1005 ± 120 | | 21.1 ± 2.1 |
| Average | | 606 ± 51 † | 0.0076 ± 0.0018 | 22.0 ± 3.9 |

TABLE 3

Comparison of lipid peroxide levels, SOD and GSH-Px activities in plus trees of Japanese cypress

| | | Sample Name | Poly-ploidy | SOD activity (unit/gr) | GSH-Px (unit/gr) | Lipid Peroxide Levels (n mol/gr) |
|---|---|---|---|---|---|---|
| Japanese Cypress (Plus Trees) | Diploids | Aso-7 | 2X | 459 ± 55 | 0.0069 ± 0.0009 | 24.4 ± 2.9 |
| | | Saeki-17 | 2X | 423 ± 54 | 0.0160 ± 0.0020 | 21.2 ± 2.7 |
| | | Hiji-4 | 2X | 544 ± 76 | 0.0019 ± 0.0002 | 23.5 ± 2.5 |
| | | Kusu-6 | 2X | 459 ± 59 | 0.0171 ± 0.0027 | 20.7 ± 2.4 |
| | | Taketa-8 | 2X | 655 ± 85 | 0.0068 ± 0.0009 | 24.0 ± 2.6 |
| | | Average | | 508 ± 78† | 0.0097 ± 0.0018 | 22.7 ± 4.3 |
| | Triploids | Misoshi-4 | 3X | 420 ± 46 | 0.0136 ± 0.0020 | 23.1 ± 2.3 |
| | | Fuji-2 | 3X | 582 ± 75 | 0.0106 ± 0.0012 | 14.1 ± 1.5 |
| | | Average | | 501 ± 76† | 0.0121 ± 0.0026 | 18.6 ± 4.1 |
| | Tetraploid | Sanko-Hinoki | 4X | 1902 ± 190 | 0.0103 ± 0.0012 | 21.5 ± 3.4 |
| | | Kiso-4X | 4X | 905 ± 99 | 0.0058 ± 0.0007 | 16.2 ± 2.5 |
| | | Average | | 1403 ± 212† | 0.0081 ± 0.0013 | 18.8 ± 2.8 |

†$P < 0.001$ (between tetraploids of plus trees of Japanese and diploids or triploids of Japanese cypress, between tetraploids of plus trees of Japanese and diploids or triploids of plus trees of Japanese cypress)

TABLE 4

Comparison of lipid peroxide levels, SOD and GSH-Px activities in plus trees of Japanese cedar, rice leaves and osmund

| | | Sample Name | Poly-ploidy | SOD activity (unit/gr) | GSH-Px activity (unit/gr) | Lipid Peroxide Levels (n mol/gr) |
|---|---|---|---|---|---|---|
| Japanese Cedar (Plus Trees) | Diploids | Naga-9 | 2X | 12 ± 1.4 | 0.0134 ± 0.0021 | 4.6 ± 0.5 |
| | | Akita-1 | 2X | 37 ± 4.4 | 0.0096 ± 0.0015 | 5.0 ± 0.6 |
| | | Saga-3 | 2X | 21 ± 2.5 | 0.0114 ± 0.0018 | 3.1 ± 0.5 |
| | | Saeki-10 | 2X | 52 ± 6.7 | 0.0104 ± 0.0015 | 4.1 ± 0.5 |
| | | Kunisaki-3 | 2X | 26 ± 2.8 | 0.0104 ± 0.0017 | 4.5 ± 0.7 |
| | | Nishikawa-2 | 2X | 17 ± 2.2 | 0.0093 ± 0.0011 | 5.0 ± 0.8 |
| | | Average | | 27 ± 3.8§ | 0.0108 ± 0.0019 | 4.3 ± 0.6 |
| | Triploids | Ooi-5 | 3X | 161 ± 19 | 0.0141 ± 0.0019 | 7.0 ± 0.8 |
| | | Kuji-30 | 3X | 41 ± 5.3 | 0.0092 ± 0.0014 | 3.7 ± 0.4 |
| | | Onta-2 | 3X | 317 ± 44 | 0.0150 ± 0.0024 | 9.5 ± 1.1 |
| | | Kyurin-3X | 3X | 108 ± 11 | 0.0182 ± 0.0023 | 8.7 ± 1.1 |
| | | Fujitsu-28 | 3X | 236 ± 28 | 0.0158 ± 0.0022 | 8.2 ± 1.2 |
| | | Miyoshi-10 | 3X | 95 ± 12 | 0.0109 ± 0.0011 | 6.1 ± 0.8 |
| | | Kuga-1 | 3X | 59 ± 8.2 | 0.0115 ± 0.0013 | 8.0 ± 1.2 |
| | | Average | | 145 ± 23‡ | 0.0135 ± 0.0021 | 7.3 ± 1.2 |
| | Tetraploid | Kanagawa-sugi | 4X | 3589 ± 430 | 0.0176 ± 0.0017 | 8.2 ± 0.9 |
| | | Cr-38 | 4X | 2684 ± 295 | 0.0128 ± 0.0020 | 9.3 ± 1.2 |
| | | Average | | 3136 ± 40‡§ | 0.0152 ± 0.0025 | 8.7 ± 1.3 |
| rice leaves | | Tosashimizu | | 2941 ± 352 | 1.3841 ± 0.1522 | 71 ± 8.5 |
| Osmund | | Tosashimizu | | 1394 ± 181 | 0.0889 ± 0.0115 | 51 ± 8.1 |

‡$P < 0.0001$ between tetraploid and triploids of plus trees of Japanese cedar.
§$P < 0.00001$ between tetraploids and diploids of plus trees of Japanese cedar.

As shown in Table 1, ultraviolet-resistant (UV-resistant) Japanese black pines was compared with ultraviolet-sensitive Japanese black pines (as control) on SOD activity, glutathione peroxidase (GSH-Px) activity and lipid peroxide levels.

In Table 2, diploids of Japanese cypress were compared with triploids with lipid peroxide levels, SOD activity and GSH-Px activity.

In Table 3, diploids, triploids and tetraploids of plus trees of Japanese cypress were compared with individual SOD activity, GSH-Px activity and lipid peroxide levels.

In Table 4, comparisons of SOD activity, GSH-Px activity, lipid peroxide level for diploids, triploids and tetra-ploids of plus trees of Japanese cedar, rice leaves and osmund. The comparison of Table 4 with Tables 5 and 6 which were described later.

The extracts from the leaves of diploid, triploid and tetraploid of Japanese cedar and Japanese cypress, were compared in Table 5 and 6 as described later. As shown in Table 5, in the column of sample added, for a mark used to description, the sample size with 0.6 gr/ml is termed as "x1" and thus 3.0 gr/ml "x2", 6.0 gr/ml "x10". In Table 6, the data of rice leaves are included for comparison.

The individual enzyme activity and lipid peroxide level for the plants described in items (1)–(3) were assayed. Testing items for measurement of enzyme activity are: SOD activity, glutathione peroxidase (GSH-Px) activity and catalase activity. The results obtained are shown in Tables 1–4. The figure is shown by mean ±SD style. On the other hand, catalase activity for those plants other than rice leaves was utterly not detectable and their results were not shown in Tables 1–4.

Regarding to the quantitative analysis of lipid peroxide level, its level was measured by using TBA reaction method of converting docohexanoic acid into TBA reactive substance.

The leaf homogenates from individual plants described above were prepared as follows and used as samples. Leaves collected were from the plant in (1)–(3). The collected leaves were powdered with a mill. The leaf homogenates from individual plants described above were used as samples. The procedure for preparation for these leaf homogenates are as follows. This powder was suspended in 95% ethanol solution for lipid peroxide formation test or in physiological saline for those tests other than lipid peroxide formation test. Both cases were at concentration of 60 mg/ml. The suspension solution was exposed to sonication (at 15W for 15 second).

After sonication, the solution was centrifuged (at 1300 g). Procedures as shown in FIG. 1, the supernatants after centrifugation were divided into two parts. One part is for the preparations of sample for lipid peroxide level dertmination. The other one was filtrated through 45 μm filter. One portion of the filtrate was used as sample for SOD activity assay and the remainded filtrates were used as sample for catalase, GSH-Px activities assays.

SOD's Quantitative Analysis

To add the mixture prepared as described above to 0.2 ml of the assay mixture containing xanthine-xanthine oxidase producing O2-, and the resulting O2-quantity was determined from reduction quantity of ferri-cytochrome c (type ∥) by the optical absorbance at 550 nm measured with a spectrophotometer (Beckman).

The quantity of SOD contained in sample is defined as the reduction quantity of reducing cytochrome c at 50% and 1 unit of SOD is expressed by unit/mg protein. In this analysis, sample itself not only inhibits the reaction on cytochrome c without the mediation of O2—, a small quantity of cytochrome c would be directly reduced. With these factors, the real SOD quantity was calculated by the formula:

$$\text{unit} = \{a - (b - c)\}/(a/2)$$

where
- a: absorbance obtained by the addition of xanthine oxidase alone.
- b: absorbance obtained by leaf homogenates in the presence of xanthine oxidase.
- c: absorbance obtained by the addition of leaf homogenate alone before the addition of xanthine oxidase.

Catalase Activity Assay

The catalase activity was determined on the velocity of reduction of hydrogen peroxide (H2O2). The velocity of reduction was measured for 12–30 seconds in the presence of leaf homogenate samples, using a spectrophotometer at 240 nm. Activity was expressed with the formula shown below.

$$K = (2.3/18) \times \log(A1/A2)$$

A1: Absorbance measured for 12 seconds at 240 nm for the assay mixture of total volume at 3.1 ml consisting 10 mmol/L H2O2 dissolving in 3 ml of 50 m mol/L potassium phosphate buffer solution and 0.1 ml of leaf homogenate.

A2: Absorbance measured for 30 seconds at 240 nm for above assay mixture

In this assay, hydrogen peroxide used as substrate may have the possibility of instability and thus substrate, hydrogen peroxide was substituted by sodium perborate. In this case, 0.002–0.05 ml leaf sample solution was suspended in 2.8 ml of 0.05 mol/L potassium phosphate buffer solution (pH 7.4), the mixture was kept at 30° C. preincubation for 5 minutes. Thereafter, to the preincubated mixture, 0.2 N sodium perborat solution was added in cuvette and the reaction was started. The data was recorded for 2–3 minutes at 220 nm.

GSH-Px Activity Assay

For GSH-Px measurement, the method of Lawrence and Burk, connecting to with oxidation of NADPH by glutathione reductase was used. The oxidation potency for NADPH was measured at 37° C. with a spectrophotometer, its wave length at 340 nm.

The assay mixture was consisted of 50 mmol/L potassium phosphate buffer solution (pH 7.0), 1 mmol/L ethylenediaminetetraacetic acid, 1 mmol/L NaN3, 0.2 mmol/L NADPH, 1 mmol/L glutathione, 2 unit of glutathione reductase, and 1.5 mmol/L cumene hydroperoxide or 10 mmol/L tert-butylperoxide solutions.

To the above mixture, leave homogenate was added to make the resulting solution volume was 1.0 ml. Thus the enzyme activity measured by this method is shown as the quantity of NADPH oxidized per minute. The activity is shown by unit/mg protein according to Lowry's method.

Lipid Peroxide Assay

The polyunsaturated fatty acid 4,7,10, 13, 16, 19-docosahexanoic acid was diluted to 200-fold in 94% ethanol. To the test tube previously poured with this substrate, then various concentration of homogenate was added and subjected to radiation with ultraviolet rays. In the experiment, homogenates of 0.6, 3.0 and 6.0 mg/ml concentration were tested. After radiation, the solution was analyzed by fluorospectrometry to measure the quantity of TBA (thiobarbituric acid). The wave length at 515 nm for excitation and at 553 nm for emission were set in an equipment of Hitachi F-2000 fluorospectrophotometer.

The result is shown with mean ±S.E. The quantity of TBA substance was adopted as lipid peroxide quantity. Furthermore, significant difference analysis was performed by Student t-test. The result of t-test demonstrates the significant difference between two groups.

Identification of Ploids of Chromosome

Poloidy of the previously described trees was determined by cytological analysis by using root ends cells or flowcytometric analysis by using leaf cells.

Discussion on Tables 1–6, was performed as follows. As shown in Tables 1–4, rice and osmund leaves (ref. Table 4) showed an apparent high SOD activity than those of gymnosperms plants such as Japanese black pines, Japanese cedar, Japanese cypress. Especially, GHS-Px of rice leaf showed as high as 1.384 unit/g and SOD activity as very high as 2941 unit/g.

As can be seen from Table 4, the SOD activity for rice leaf is higher than those of individual trees tested (except Japanese cedar, a tetraploid plant), and in some cases, the highest SOD activity, showed a 100-fold activity of individual ordinary tree tested. In Table 4, osmund leaf also showed the SOD activity as high as 1394 unit/g.

Gymnosperms plants as the test subject, as shown in Table 1 ($P<0.01$), Japanese black pines possessing ultraviolet-resistant property, its SOD activity is found to be apparently higher than the ordinary Japanese black pines. For example, the SOD activity of the Japanese black pines possessing ultraviolet-resistant property is 413±56 unit/g on average, and it is much higher 240±37 unit/g on average of the ordinary Japanese black pines.

From the above results, it is ascertained that in the case the tree possesses the ultraviolet-resistant properties, the tree has high SOD activity. This may suggest that SOD activity play a role to protect them from damage of ultraviolet rays.

When comparing the SOD activity of triploid species tree and tetraploid species tree, as shown in Tables 2–3, especially in the individual trees, the tetraploid species tree showed a higher SOD activity than triploid species tree. The plus tree of the Japanese cedar (sample name Kamikawa cedar, Cr-38c) as shown in Table 4, showed a very high SOD activity than those ordinary trees. In such Japanese cedar, the apparent increase of SOD activity was found in trees possessing tetraploid chromosome. In contrast to this, both diploid and triploid trees showed no apparent increase of SOD activity.

Secondly, as to the lipid peroxide level, it was demonstrated that those cedars with small quantity of resin have a very little lipid peroxide formation ability compared with other trees.

The difference of GSH-Px activity between ultraviolet-resistant Japanese black pines and ultraviolet-sensitive ordinary Japanese black pines as control in Table was not found (refer to Table 1, $P>0.05$). This may suggest that no relationship of GSH-Px enzymes with ultraviolet resistance.

TABLE 5

Comparison of SOD activity and the effect of lipid peroxidation by the extract of leaves among 2X, 3X and 4X in Japanese trees

| Samples | Polyploidy | SOD Activity (unit/gr) | Sample added | Lipid peroxidation average UV (−) control 45 UV (+) control 260 % control |
|---|---|---|---|---|
| S-20 | 2X | 133 ± 15 | x1* (0.6 mgr/ml) | 124.6 ± 14.9 |
|  |  |  | x5* (3.0 mgr/ml) | 73.3 ± 9.5 |
|  |  |  | x10* (6.0 mgr/ml) | 33.8 ± 4.7 |
| S-22 | 2X | 149 ± 17 | x1 | 115.3 ± 13.8 |
|  |  |  | x5 | 71.4 ± 9.2 |
|  |  |  | x10 | 31.5 ± 4.4 |
| S-23 | 2X | 421 ± 54 | x1 | 221.5 ± 24.3 |
|  |  |  | x5 | 137.9 ± 17.9 |
|  |  |  | x10 | 60.3 ± 7.2 |
| S-25 | 3X | 629 ± 81 | x1 | 174.6 ± 19.2 |
|  |  |  | x5 | 112.5 ± 14.6 |
|  |  |  | x10 | 63.9 ± 10.2 |
| S-26 | 3X | 2173 ± 260 | x1 | 82.7 ± 10.7 |
|  |  |  | x5 | 62.1 ± 9.9 |
|  |  |  | x10 | 43.6 ± 5.2 |
| S-28 | 3X | 309 ± 33 | x1 | 150.6 ± 24.0 |
|  |  |  | x5 | 89.2 ± 13.3 |
|  |  |  | x10 | 41.9 ± 6.7 |
| S-30 | 4X | 1382 ± 193 | x1 | 84.2 ± 10.9 |
|  |  |  | x5 | 62.3 ± 8.7 |
|  |  |  | x10 | 42.7 ± 4.6 |
| S-31 | 4X | 1447 ± 231 | x1 | 79.4 ± 10.3 |
|  |  |  | x5 | 57.3 ± 9.1 |
|  |  |  | x10 | 37.1 ± 5.1 |
| S-32 | 4X | 1096 ± 164 | x1 | 72.9 ± 9.4 |
|  |  |  | x5 | 61.4 ± 7.9 |
|  |  |  | x10 | 51.9 ± 8.3 |
| S-33 | 4X | 1237 ± 160 | x1 | 71.6 ± 12.1 |
|  |  |  | x5 | 49.8 ± 6.4 |
|  |  |  | x10 | 38.4 ± 6.1 |
| S-34 | 4X | 1645 ± 213 | x1 | 86.0 ± 11.1 |
|  |  |  | x5 | 64.1 ± 9.6 |
|  |  |  | x10 | 44.1 ± 7.0 |
| S-36 | 4X | 1105 ± 154 | x1 | 140.1 ± 15.4 |
|  |  |  | x5 | 94.8 ± 15.1 |
|  |  |  | x10 | 53.7 ± 6.9 |
| S-38 | 4X | 1046 ± 135 | x1 | 136.6 ± 19.1 |
|  |  |  | x5 | 111.6 ± 15.6 |
|  |  |  | x10 | 89.0 ± 10.6 |

*x1 denotes 0.6 gr/ml as unit and the column "sampl added" shows multiple of the unit

TABLE 6

Comparison of SOD activity and the effect of lipid peroxidation by the extract of leaves among 2X, 3X and 4X in Japanese trees

| Samples | Polyploidy | SOD activity (unit/gr) | Sample added | Lipid peroxidation Average UV (−) control 45 UV (+) control 260 % control |
|---|---|---|---|---|
| H-1 | 2X | 160 ± 19 | x1* (0.6 mgr/ml) | 163.0 ± 17.9 |
|  |  |  | x5* (3.0 mgr/ml) | 98.2 ± 11.7 |
|  |  |  | x10* (6.0 mgr/ml) | 58.5 ± 7.6 |
| H-2 | 2X | 352 ± 45 | x1 | 151.8 ± 21.2 |
|  |  |  | x5 | 103.4 ± 11.3 |
|  |  |  | x10 | 56.8 ± 6.2 |
| H-5 | 3X | 578 ± 80 | x1 | 170.0 ± 22.1 |
|  |  |  | x5 | 114.3 ± 17.1 |
|  |  |  | x10 | 60.8 ± 7.2 |
| H-6 | 3X | 1066 ± 138 | x1 | 95.2 ± 13.3 |
|  |  |  | x5 | 53.1 ± 6.3 |
|  |  |  | x10 | 45.2 ± 5.8 |

TABLE 6-continued

Comparison of SOD activity and the effect of lipid peroxidation by the extract of leaves among 2X, 3X and 4X in Japanese trees

| Samples | Polyploidy | SOD activity (unit/gr) | Lipid peroxidation Average UV (−) control 45 UV (+) control 260 Sample added | % control |
|---|---|---|---|---|
| H-7 | 3X | 742 ± 89 | x1 | 139.1 ± 15.3 |
|  |  |  | x5 | 87.6 ± 10.5 |
|  |  |  | x10 | 40.4 ± 4.4 |
| H-8 | 3X | 821 ± 106 | x1 | 123.6 ± 14.8 |
|  |  |  | x5 | 78.4 ± 9.4 |
|  |  |  | x10 | 38.1 ± 4.9 |
| H-9 | 3X | 1280 ± 140 | x1 | 92.5 ± 12.9 |
|  |  |  | x5 | 62.3 ± 6.9 |
|  |  |  | x10 | 39.0 ± 4.6 |
| H-10 | 4X | 1773 ± 265 | x1 | 52.6 ± 6.8 |
|  |  |  | x5 | 37.8 ± 6.0 |
|  |  |  | x10 | 25.3 ± 3.5 |
| H-11 | 4X | 1232 ± 172 | x1 | 90.8 ± 12.7 |
|  |  |  | x5 | 61.4 ± 7.9 |
|  |  |  | x10 | 32.3 ± 4.8 |
| rice leaves |  | 2941 ± 352 | x1 | 455.2 ± 54.6 |
|  |  |  | x5 | 298.3 ± 38.7 |
|  |  |  | x10 | 165.0 ± 21.4 |

*x1 denotes 0.6 gr/ml as unit and the column "sampl added" shows multiple of the unit Lipid peroxide formation was enhanced at low concentration of homogenate (e.g. 0.6 mg/ml) and a high concentration of homogenate inhibited the formation of lipid peroxide. This is clearly shown in Tables 5 and 6.

As shown in Tables 5 and 6, when tetraploid tree leaf samples are compared each other, it is clear that in those samples of high SOD activity whose inhibitory effects is strong in presence of low sample concentration. This may suggest that SOD activity plays a role to inhibit formation of the lipid peroxide as cytotoxic role. This means that the higher SOD activity, the more extensive inhibition on the lipid peroxide formation.

For example, Japanese cedar sample nos. S-26, -30, -32, -34, -36-38 in Table 5 and Japanese cypress samples nos. H-6, -9, -10, -11 in Table 6, have higher SOD activity than 1,000 unit/g. Among them, nine cases: sample nos. S-26, -30, -32, -34; H-6, -9, -10, showed a lower lipid peroxide formation (indicating in column of x1 of Table 5) with addition of low sample concentration than controls.

In the case of rice leaf's sample, the formation of lipid peroxide was inhibited regardless of low concentration of homogenate (see "x1 column" of Table 5) or high concentration (see "x10 column" of Table 5). Thus SOD activity demonstrated a high activity as those of GHS-Px activity and catalase activity. Among the leaf samples tested, the rice leaf showed the highest level for lipid peroxide formation. Samples other than rice leaf, their catalase activities were not detectable and thus data are not included in Tables.

On the other hand, the higher SOD activity, the stronger anti-oxidation effects are known as usual. The SOD plays an important role of removal of active oxygen.

Upon consideration on factors in relating to formation of active oxygen, the existence of ultraviolet rays is not neglected. In recent years, destruction of ozonosphere involved with increase of ultraviolet radiation forwarding to earth. Based on this evidence, apparent increase of oxygen radical had been identified. Like human beings, trees Occur withering uprightly when exposing to ultraviolet rays and succeedingly to high concentration of oxygen radical.

But according to the experimental results that SOD activity are high, as obtained by the present inventors for those trees possessing ultraviolet resistance, they are thought to play a function to protect themselves from the damage exerted from environment by using the anti-oxidization agents such as SOD containing in their leaves. Until now, no reports concerning the self-protection against the environmental damage, by trees using anti-oxidization agent possessed in the trees. This is the new finding by the present inventors.

The anti-oxidization ability of ultraviolet-resistant pine tree (hereinafter abbreviated as "UV-resistant") was compared with that of ordinary pine tree. Usually, reports on induction of GHS-px activity in response to oxygen radical were available. But in the experiments performed by the present inventors, no result on apparent change of GHS-px activity paralleled to SOD activity was not established.

Regarding to catalase, there was a report dealt with the occurrence of catalase induced by the oxygen radicals in tree. But in the present experiment found no occurrence of catalase except for rice leaves. This may be considered that terpene, etc in the homogenates inhibits the activation.

It is well known that like the enzymes such as superoxidase, the low molecular weight substances for example, vitamin C as oxidizing agent, plays a major role in trees. With the experiment in this invention, study on anti-oxidization function of low molecular weight compound was not performed but those on SOD activity performed. It is concluded that SOD, a strong anti-oxidizing enzyme is occurring in the tree leaves for protecting itself against excessive oxygen radicals.

Further to the above discussions, when considering the relationship of SOD activity and chromosomes of plants, those trees possessing triploid and tetraploid, especially the tetraploid trees, have a high SOD activity as discovered by the present inventors. There was no discussion on the relationship between extent of SOD activity and ploid of tree done by others, and thus the results obtained by the present inventors as mentioned above are utterly beyond estimation.

When consider on the relationship of SOD activity and multiploid of chromsome, an increase of locus of chromosome encoding SOD, this brings the increase of SOD quantity existing. This consideration may be affirmative as referring to the evidence for example, in human beings, Down's syndrome was found to have three chromosomes (trysomy) containing Cu,Zn-SOD loci and this leading to an increase by 50% of SOD quantity.

Though the increase of SOD activity found in the trees of triploid and of tetraploid individually, in the experiments performed by the present inventors, an promoting level of SOD itself was not confirmed. This is to say that another elucidation may be applicable to consider, however It is concluded that locus of SOD chromosome is not found to increase in the individual sample tested.

And rice leaves are thought to possess the ultraviolet light resistance, its SOD activity was found to be not only high than those of Japanese cedar, black pine and plus tree of Japanese cypress, but also showed a high GHS-Px acitity than the trees. Furthermore, catalase was hardly detectable in the trees, rice leaves showed a detectable level.

Namely, with an ability that a strong enzyme activity possessed by the tree in response to the environmental oxygen radical and ultraviolet rays, the monocotyledonous plants can acquire the high adaptability against environmental ultraviolet rays. For example, a fern is more primitive plant than gymensperms and angiosperms, and it is well known that a fern acquire the high adaptability by multiplying their chromosome number to multiploid. Improving adaptability against the environmental perturbation by acquiring multiploid fact is also reported recently in bacteria.

Furthermore, from the experiments described above, in the Japanese cedar, Japanese cypress possessing ultraviolet-resistant properties were proved to have triploid and tetraploid of chromosomes. While even those ultraviolet-sensitive gymensperms, strengthen their SOD activity by multiplying their ploid of chromosome, to protect themselves in response to the increased exposing time to ultraviolet rays and oxygen radical. This is to say that the species appeared to have adaptability is considerable.

On the other hand, it is considerable that UV-resistant black pine tree increases SOD to protect itself without the relationship of multiploid of chromosome in contrast to the ordinary black pine tree. It is also thought that the UV-resistant black pine tree does not adopt the measure to be taken for multiplying its chromosome into multiploid. As a general thinking, the increased UV-B (B region ultraviolet rays distributes in 280 nm–320 nm) radiation is known to be not connected to damage of oxidation to the bodies such as plants, etc. Thus the case of black pine tree is corresponding to this hypothesis.

There two types on acquisition of multiploid of chromosome by plants: one type is natural or artificial cross, the other one is nature mutation such as branch change type or the artificial mutation with colchicines treatment.

Osmunda, a fern, comparing to gymnesperms and angiosperms plants, many kinds of fern already acquired multiploid. It is well known that monocytoledonous plants such as rice etc. possess the ultraviolet resistance than the black pine, Japanese cedars and Japanese cypress. The experiments performed by the present inventors indicate that both osmunda and the rice leaves showed a stronger SOD activity than other trees. Gymnsperms plants such as black pine, Japanese cedars, and Japanese cypress, etc., should to demonstrate their actions in response to the real environment by multiplying their chromosome having SOD gene, as the present inventors observed so.

From survey of references on agriculture and gardening field, it is confirmed that in the field of improvement of kind of plants such as green tea, apple, banana, tulip, orchid etc, polyploid is used in many cases. But in the conventional Japanese cedar, Japanese cypress, etc, the multiploid species are found to grow not so good as the ordinary diploid species. This value of multiploid species was utterly not noticed by the forestry industries.

In the plus tree of Japanese cedars and Japanese cypress, the present inventors found out the natural triploid species among the sterile species with cell biological research. The reports together with the results obtained by present inventors, reveal that only 41 clones of Japanese cedars and two clones of plus tree of Japanese cypress were found to be the triploid species, respectively. By the way, "plus tree" is a kind of trees shows a good growth character.

The present inventors made an effort to breed the species of triploid by using artificial crossing technology. The effort was performed by crossing between diploid and tetraploid species in Japanese cedar and Japanese cypress, respectively. The artificial triploid species bred thus obtained by artificial crossing, were confirmed to grow better than diploid species by the present inventors.

Namely, a better growth of aritificial crossing triploid species was confirmed than the conventional triploid one. This is concluded that it is possible and beneficial to use the multiploid to breed Japanese cedar and Japanese cypress.

Furthermore in the lipid peroxide assay, the leave homogenate of tetraploid containing a high SOD activity, apparently inhibited the lipid peroxide formation. This evidence may suggest that trees protect themselves from the damage by oxygen radicals introduced by ultraviolet rays through multiplying their chromosomal number.

Those Japanese cedars except tetraploid cedar, containing comparatively small resin than other trees, showed a low lipid peroxide Level and low SOD activity. Such results were identified in Tables 2–4. Because this Japanese cedar contains small resin, it is clear that the formed lipid peroxide can be estimated to be small. This means that treatment of low lipid peroxide formation, a low SOD activity is considered to be enough.

Namely, it is considered that Japanese cedar not needs to use high SOD activity to treat the low lipid peroxide, because, cedar tree does not produce the quantity of lipid peroxide.

According to the research of present inventors, it was confirmed that trees show an excellent adaptability against the increase of harmful oxygen radicals occurring due to the recent acceleration tendency of ozonosphere damage. A fern, an evolutionary more primitive plant than gymnosperms and angiosperms plants, acquired multiploid as its adaptability against the disadvantage of environmental perturbations by multiplying chromosome number.

Also in those needle-leaved plants such as Japanese cedar and Japanese cypress, it is found that their seedlings acquired the ultraviolet resistant property by multiplying their chromosome number in the comparison of the ultraviolet resistant species with the ultraviolet non-resistant species. Especially, triploid, tetraploid trees were found to have this tendency.

On the other hand, although some species with natural cross, grew not good or became sterile, it is confirmed that some species obtain a good growth characteristics by artificial cross.

Namely, for Japanese cedar, Japanese cypress, etc. the means to acquire adaptability by multiplying ploid into multiploid were found to be adoptable. This production of multiploid descendants by artificial crossing etc. can be said as the effective method to protect trees from increasing tendency of oxygen radicals induced by ultraviolet rays.

This invention is not necessary to limit to the form of above examples, all the examples if not separated from the object of this invention is termed as within the range of this invention.

For example, the above needle-leaved trees such as Japanese cedar, Japanese cypress were explained and this will be considered also to apply to the broad-leaved trees. And this also be considered to apply to evergreen trees, and deciduous trees. On the other hand, on the evidence that trees acquired the ultraviolet rays resistance by multiplying their chromosome number, though this experiment was not obtained in Japanese black pine tree, there might of course be some species of Japanese black pine trees that acquired the ultraviolet rays resistance through obtaining the multiploid means, because there are many kinds of pine trees.

It is considered that the strong plant species of ultraviolet resistance can be selected from the standard of ploid of chromosome. And the selected plants are planted in the plenty sunshine area to keep the strong ultraviolet rays resistance plant ecology, this means are considered to be the positive protection of plant ecological environment in the area.

Though the above explanation is focused on the triploid and tetraploid, Those multiploid trees such as pentploid and hexaploid chromosomes will be the same result obtainable.

In the man-planted forest of the present invention, damages such as death of trees caused by ultraviolet rays are significantly inhibited Accordingly, if the scale of ultraviolet radiation on the earth increases due to the progression of destruction of the ozonosphere the man-planted forest of the present invention will reliably be remained. By employing the method of planting trees of the present invention, a man-planted forest having such resistance to ultraviolet can be formed.

What is claimed is:

1. A method of planting trees, comprising the steps of:
   selecting conifer seedlings having a tetraploid chromosome number;
   determining which of the selected conifer seedlings exhibit resistance to ultraviolet rays; and
   planting in a forest only the selected seedlings which exhibit resistance to ultraviolet rays.

2. The method of planting trees according to claim 1, wherein the conifer seedlings are cedar or cypress.

3. The method of planting trees according to claim 1, further comprising the step of obtaining the chromosome number of the seedlings by increasing the basic number of chromosomes.

4. The method of planting trees according to claim 3, wherein the basic number of chromosomes is increased by mutation.

5. The method of planting trees according to claim 3, wherein the basic number of chromosomes is increased by breeding.

6. The method of planting trees according to claim 1, wherein the step of determining which of the selected conifer seedlings exhibit resistance to ultraviolet rays involves analyzing activity of an anti-oxidation agent in leaves of the seedlings.

7. The method of planting trees according to claim 1, wherein the step of determining which of the selected conifer seedlings exhibit resistance to ultraviolet rays involves analyzing activity of SOD in leaves of the seedlings.

8. A method of growing plants, comprising the step of:
   artificially forming vegetation which is significantly resistant to ultraviolet rays, as compared with vegetation constituted of diploid plants, by selectively growing plants whose chromosone number is tetraploid and thus exceeds the basic number of the species and which exhibit resistance to ultraviolet rays.

9. The method of growing plants accordig to claim 1, further comprising the step of determining which of the plants exhibit resistance to ultraviolet rays.

10. The method of growing plants according to claim 9, wherein the step of determining which of the plants exhibit resistance to ultraviolet rays involves analyzing activity of an anti-oxidation agent in leaves of the plants.

11. The method of planting trees according to claim 9, wherein the step of determining which of the plants exhibit resistance to ultraviolet rays involves analyzing activity of SOD in leaves of the plants.

* * * * *